United States Patent [19]
Fürst et al.

[11] 4,057,561
[45] Nov. 8, 1977

[54] D-HOMO-19-NORSTEROIDS

[75] Inventors: Andor Fürst, Basel; Jürg Gutzwiller, Bettingen; Marcel Müller, Frenkendorf, all of Switzerland; Rudolf Wiechert, Berlin, Germany; Ulrich Eder, Berlin, Germany; Günter Neef, Berlin, Germany

[73] Assignee: Hoffmann-La Roche Inc., Nutley, N.J.

[21] Appl. No.: 770,433

[22] Filed: Feb. 22, 1977

[30] Foreign Application Priority Data

Feb. 23, 1976  Austria ............................ 1269/76
Jan. 3, 1977   Switzerland ........................ 2/77

[51] Int. Cl.² .......... C07C 49/48; C07C 69/02; C07D 309/22
[52] U.S. Cl. .......... 260/345.9 S; 260/295.5 P; 260/345.8 R; 260/347.5; 260/586 E; 260/617 A; 260/617 F; 424/266; 424/285; 424/283; 424/308; 424/311; 424/331; 424/343; 560/108; 560/105; 560/139; 560/51; 560/124; 560/122
[58] Field of Search .......... 260/586 E, 488 B, 617 F, 260/345.9, 476 C, 295.5 Q, 345.8, 347.5, 617 A

[56] References Cited
U.S. PATENT DOCUMENTS 3,984,476  10/1976  Fürst et al. ............... 260/586 E

FOREIGN PATENT DOCUMENTS 826,077   8/1975  Belgium ................. 260/586 E
2,274,308 1/1976  France .................. 260/586 E
2,452,907 6/1975  Germany ................. 260/586 E
2,404,130 8/1974  Germany ................. 260/586 E Primary Examiner—Gerald A. Schwartz
Attorney, Agent, or Firm—Samuel L. Welt; George M. Gould; Raymond R. Wittekind

[57] ABSTRACT

D-homosteroids of the formula

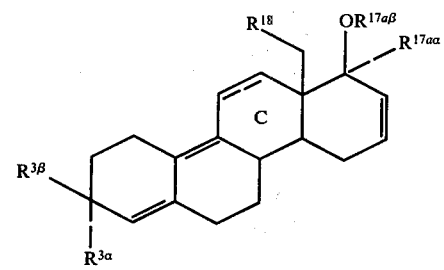

wherein $R^{3\alpha}$ is hydrogen, $R^{3\beta}$ is hydroxy, lower alkanoyloxy or aroyloxy and $R^{3\alpha}$ and $R^{3\beta}$ taken together are oxo; $R^{17a\alpha}$ is hydrogen, lower alkyl, ethynyl, vinyl, allyl, methallyl, propadienyl, 1-propynyl, butadiynyl or chloroethynyl; $R^{17a\beta}$ is hydrogen, alkanoyl, aroyl, lower alkyl, cycloalkyl-lower-alkyl, benzyl, furfuryl or tetrahydropyranyl; $R^{18}$ is hydrogen or methyl and the dotted line in the C-ring denotes an additional carbon to carbon bond in the 11,12-position and processes for the preparation thereof are disclosed.

The D-homosteroids of the present invention are useful as ovulation inhibitors and androgenic/anabolic agents.

16 Claims, No Drawings

D-HOMO-19-NORSTEROIDS

DESCRIPTION OF THE INVENTION

The present invention relates to novel D-homosteroids of the formula

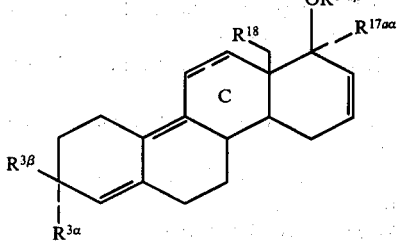

(I)

wherein $R^{3\alpha}$ is hydrogen, $R^{3\beta}$ is hydroxy, lower alkanoyloxy or aroyloxy and $R^{3\alpha}$ and $R^{3\beta}$ taken together are oxo; $R^{17a\alpha}$ is hydrogen, lower alkyl, ethynyl, vinyl, allyl, methallyl, propadienyl, 1-propynyl, butadiynyl or chloroethynyl; $R^{17a\beta}$ is hydrogen, alkanoyl, aroyl, lower alkyl, cycloalkyl-lower-alkyl, benzyl, furfuryl or tetrahydropyranyl; $R^{18}$ is hydrogen or methyl and the dotted line in the C-ring denotes an additional carbon to carbon bond in the 11,12-position.

The D-homosteroids of formula I can be prepared in accordance with the invention by a. isomerizing or dehydrogenating and isomerizing a D-homosteroid of the formula

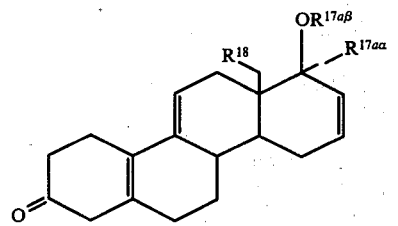

II wherein $R^{17a\alpha}$, $R^{17a\beta}$ and $R^{18}$ are as above by treatment with an acid, a base or a p-quinone; or b. reacting a D-homosteroid of the formula

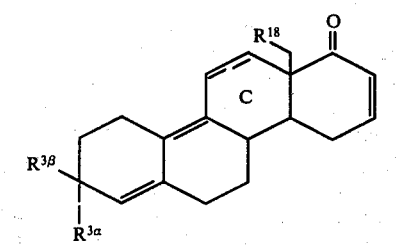

III wherein $R^{3\alpha}$, $R^{3\beta}$, $R^{18}$ and the dotted line in the C-ring are as above,
with an organometallic compound donating the $R^{17a\alpha}$ radical, with intermediate protection of a 3-keto group, if present; or c. treating a D-homosteroid of the formula

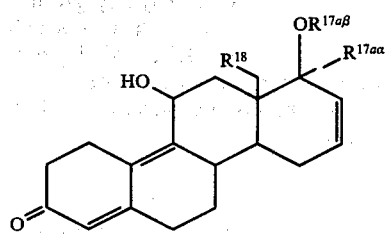

IV wherein $R^{17a\alpha}$, $R^{17a\beta}$ and $R^{18}$ are as above,
with an acid; or d. treating a D-homosteroid of the formula

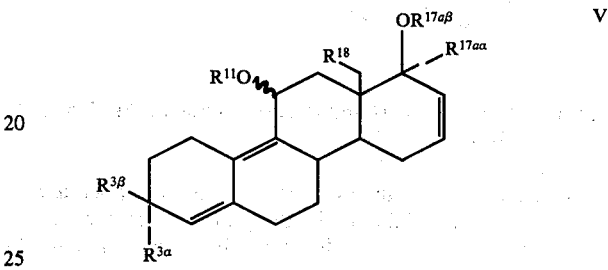

V wherein $R^{3\alpha}$, $R^{3\beta}$, $R^{17a\alpha}$, $R^{17a\beta}$ and $R^{18}$ are as above and $R^{11}$ is sulfonyl,
with a base; or e. treating a D-homosteroid of the formula

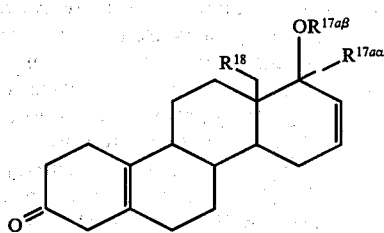

VI wherein $R^{17a\alpha}$, $R^{17a\beta}$ and $R^{18}$ are as above with pyridinium bromide perbromide in the presence of an organic base; or f. acylating or alkylating the hydroxy group(s) in the 17a-position in a D-homosteroid of formula I in which at least one hydroxy group is present in the 3- and/or 17a-position, or g. reducing the 17a-keto and/or the 3-keto group to a hydroxy group in a D-homosteroid of the formula

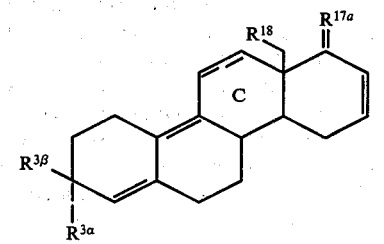

VII in which $R^{3\alpha}$, $R^{3\beta}$ and the dotted line in the C-ring are as above and $R^{17a}$ represents oxo or ($OR^{17a\beta}$, $R^{17a\alpha}$) wherein $R^{17a\alpha}$ and $R^{17a\beta}$ are as above
and at least one keto group is present in position 3 or 17a if desired, with intermediate protection of a 3- or 17a-keto group when both $R^{17a}$ and $R^{3\alpha}$ and $R^{3\beta}$ taken together are oxo; or h. saponifying the 17a-alkanoyloxy or aroyloxy groups and a 3-alkanoyloxy or aroyloxy group, if present, in a D-homosteroid of formula I in which $R^{17a\beta}$ represents alkanoyl or aroyl, $R^{3\alpha}$, $R^{3\beta}$, $R^{17a\alpha}$ and the dotted line in the C-ring are as above; or i. hydrogenating the ethynyl group in a D-homosteroid of the formula

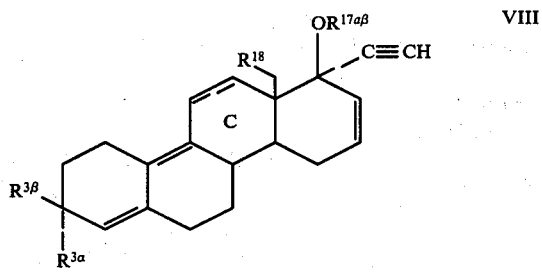

wherein $R^{3\alpha}$, $R^{3\beta}$, $R^{17a\beta}$ and the dotted line in the C-ring are as above
to a vinyl group.

As used throughout the specification and appended claims, the term "alkanoyl" denotes the residue obtained by removal of the hydroxy function of alkane- and cycloalkanecarboxylic acids. Examples of alkanoyl groups are acetyl, propionyl, butanoyl, valeryl, caproyl, oenanthyl, oxalyl, succinyl, citroyl, cyclopentylpropionyl, cyclohexylacetyl, cyclopropylacetyl, cyclopropylcarbonyl, cyclopentylcarbonyl and cyclohexylcarbonyl. The term "aroyl" denotes the residue obtained by removal of the hydroxy function of aromatic carboxylic acids. Examples of aroyl groups are benzoyl, phenylacetyl, phenoxyacetyl and nicotinoyl. The term "alkyl" denotes straight-chain or branched-chain hydrocarbon groups. Examples are methyl, ethyl, propyl, isopropyl, butyl and isomers thereof. The term "sulfonyl" denotes the residue obtained by removal of the hydroxy function of sulfonic acids. Examples of sulfonyl groups are methanesulfonyl, ethanesulfonyl, phenylsulfonyl and 4-tolylsulfonyl. The term "alkanoic acid" denotes an alkanecarboxylic acid. Examples of alkanoic acids are formic acid, acetic acid, propionic acid, butyric acid, valeric acid, caproic acid and oenanthic acid. The term "lower" denotes the numerical range of 1 to 7. The preferred lower alkyl residues are methyl and ethyl.

In the formulas presented herein the various substituents are illustrated as joined to the steroid nucleus by one of two notations: a solid line (—) indicating a substituent which is in the β- orientation (i.e., above the plane of the molecule) and a broken line ( - - - ) indicating a substituent which is in the α-orientation (i.e., below the plane of the molecule). The formulas have all been drawn to show the compounds in their absolute stereochemical configuration. Inasmuch as the starting materials, as well as the final products, are derived from naturally occurring materials, they exist in the single absolute configuration depicted herein. The processes of the present invention, however, are intended to apply as well as to the synthesis of steroids of the racemic series.

A preferred group of D-homosteroids of formula I are those compounds wherein $R^{3\alpha}$ and $R^{3\beta}$ taken together represent oxo and the C-ring contains a double bond. Those compounds of formula I wherein $R^{17a\alpha}$ is hydrogen, methyl or ethynyl and $R^{17a\beta}$ is hydrogen, lower-alkanoyl, lower-alkyl or benzyl and also preferred. Of particular interest are the 17a-hydroxy-D-homo-19-nor-17aα-pregna-4,9,11,16-tetraen-20-yn-3-one and the 17aβ-hydroxy-17a-methyl-D-homoestra-4,9,11,16-tetraen-3-one. Further Examples of compounds of formula I are 1. 13-Ethyl-17a-hydroxy-D-homo-18,19-dinor-17aα-pregna-4,9,11,16-tetraen-20-yn-3-one;
2. 17a-Hydroxy-D-homo-19-nor-17aα-pregna-4,9,16-trien-20-yn-3-one;
3. 13-Ethyl-17a-hydroxy-D-homo-18,19-dinor-17aα-pregna-4,9,16-trien-20-yn-3-one;
4. 17aβ-Hydroxy-D-homo-19-norestra-4,9,11,16-tetraen-3-one;
5. 13-Ethyl-17aβ-hydroxy-D-homogona-4,9,11,16-tetraen-3-one;
6. 13-Ethyl-17aβ-hydroxy-17a-methyl-D-homogona-4,9,11,16-tetraen-3-one;
7. 17aβ-Benzyloxy-D-homoestra-4,9,11,16-tetraen-3-one;
8. 13-Ethyl-17aβ-benzyloxy-D-homogona-4,9,11,16-tetraen-3-one;
9. 17aβ-Amyloxy-D-homo-19-norestra-4,9,11,16-tetraen-3-one;
10. 13-Ethyl-17aβ-amyloxy-D-homogona-4,9,11,16-tetraen-3-one;
11. 17aβ-Acetoxy-D-homoestra-4,9,11,16-tetraen-3-one;
12. 13-Ethyl-17aβ-acetoxy-D-homogona-4,9,11,16-tetraen-3-one;
13. 17aβ-(Cyclohexyl)methoxy-D-homo-19-norestra-4,9,11,16-tetraen-3-one;
14. 13-Ethyl-17aβ-(cyclohexyl)methoxy-D-homo-19-norgona-4,9,11,16-tetraen-3-one.
15. 17aα-Ethynyl-3β,17a-dihydroxy-D-homoestra-4,9,11,16-tetraen;
16. 3β,17aβ-Diacetoxy-17a-ethynyl-13-ethyl-D-homogona-4,9,11,16-tetraene;
17. 3β,17aβ-Dihydroxy-D-homoestra-4,9,11,16-tetraene;
18. 3β,17aβ-Dihydroxy-13-ethyl-D-homogona-4,9,11,16-tetraene;
19. 3β,17aβ-Diacetoxy-17a-ethynyl-13-ethyl-D-homogona-4,9,11,16-tetraene;
20. 3β,17aβ-Dihydroxy-17a-methyl-D-homoestra-4,9,11,16-tetraene;
21. 13-Ethyl-3β,17aβ-dihydroxy-17a-methyl-D-homogona-4,9,11,16-tetraene.

The reaction of a compound of formula II with a substituted p-quinone according to process variant (a) leads to a compound of formula I in which an additional double bond in the 11,12-position of the C-ring is present. Suitable substituted p-quinones are, in particular, p-benzoquinones, such as 2,3-dichloro-5,6-dicyano-benzoquinone (DDQ), chloranil, 2,3-dibromo-5,6-dicyanobenzoquinone, 2,3-dicyano-5-chlorobenzoquinone and 2,3-dicyano-benzoquinone. The reaction is appropriately carried out in an organic solvent, e.g., halogenated hydrocarbons, such as chlorobenzene and methylene chloride, ethers such as diethyl ether, dioxane and diethylene glycol diethyl ether, hydrocarbons such as benzene and toluene, and esters such as ethyl acetate. The reaction may be carried out at room temperature or at elevated temperatures; the reaction is preferably carried out under an inert gas.

In another embodiment of process variant (a), a compound of formula II is treated with an acid or a base, a compound of formula I being obtained in which the additional double bond in the 11,12-position of the C-ring is absent, i.e., compounds in which the C-ring is saturated. Suitable acids for this reaction are strong acids such as mineral acids, e.g., methanolic hydrochloric acid, sulfuric acid and perchloric acid, and sulfonic acids such as p-toluenesulfonic acid; suitable bases are, e.g., inorganic bases such as alkali metal and alkaline earth hydroxides and carbonates and organic bases such as pyridine and triethylamine. The use of acids is preferred.

The reaction of the $R^{17a}$ keto group of a compound of formula III with an organometallic compound according to process variant (b) can also be carried out by a known method. The organometallic compound may be a Grignard compound, e.g., ethynylmagnesium bromide, methylmagnesium bromide, vinylmagnesium bromide, or an alkali organometallic compound such as sodium, potassium or lithium acetylide and vinyllithium. A simultaneously present 3-keto group may be intermediately protected as, e.g., a ketal, enol ether or enamine.

In process variant (c), a compound of formula IV is heated with an acid, e.g., a sulfonic acid such as p-toluenesulfonic acid, a mineral acid such as hydrochloric acid, or preferably, formic acid to afford a compound of formula I in which the C-ring is unsaturated. This process variant is appropriately applied in the preparation of those D-homosteroids of formula I which do not contain acid-sensitive groups such as a $17a\beta$-hydroxy-$17a\alpha$-methyl moiety.

Examples of sulfonyl radicals $R^{11}$ in the starting materials for process variant (d) are methanesulfonyl and p-toluenesulfonyl. Suitable bases are organic bases such as pyridine, collidine and triethylamine.

Suitable organic bases for process variant (e) are, e.g., pyridine, collidine and triethylamine. Preferably, pyridine is employed and the reaction is performed at about 0° C to about room temperature.

The acylation of a free hydroxy group in the 3- or 17a-positions in a D-homosteroid of formula I may be carried out by treatment with a reactive acid derivative, e.g., an acid halide or acid anhydride, in the presence of a base such as pyridine, collidine or 4-diethylaminopyridine.

The reduction of a 3- or 17a-keto group according to process variant (g) may be carried out in a known manner by means of complex metal hydrides, e.g., di-(lower alkyl)-aluminum hydrides such as di-isobutylaluminum hydride, lithium aluminum hydride, sodium aluminum hydride and sodium borohydride and trimethoxy- or tributoxy-lithium aluminum hydride. Suitable solvents for this reaction are hydrocarbons, e.g., cyclohexane, benzene and toluene and ethers, e.g., diethyl ether and tetrahydrofuran. When a 17a-keto group is to be reduced in the presence of a 3-keto group and vice versa, the 3-keto group or the 17a-keto group is intermediately protected. The introduction and the removal of such protective groups can be accomplished by known methods.

The saponification of 17a- and 3-alkanoyl- and aroyloxy groups in process variant (h) may be accomplished by known methods. Alkanoyl- and aroyloxy groups may be saponified, e.g., with aqueous-alcoholic bases such as aqueous-methanolic potassium carbonate. The hydrogenation of the ethynyl group according to process variant (i) may be conducted in the presence of noble metal catalysts such as palladium-calcium carbonate and, preferably, a deactivator such as pyridine.

The starting materials for the preparation of the compounds of the present invention of formula I may, if they are unknown or their preparation is not described herein, be prepared by known methods or methods analogous to those described below.

The compounds of formula I are hormonally active. In particular, compounds of formula I in which $R^{17a\alpha}$ represents unsaturated radicals exhibit progestational activity. For example, in the Clauberg Test, the McPhail value of 17a-hydroxy-D-homo-19-nor-17a$\alpha$-pregna-4,9,11,16-tetraen-20-yn-3-one is 3.5 at 50 mg/kg per os and 2.8 at 20 mg/kg (subcutaneous). These compounds are useful as ovulation inhibitors. Compounds of formula I in which $R^{17a\alpha}$ denotes hydrogen or lower alkyl can be used as androgenic/anabolic agents. In the muscle levator ani-Test, 17a$\beta$-hydroxy-D-homo-estra-4,9,11,16-tetraen-3-one was, on subcutaneous application, about 3 times more active than testosterone propionate.

The compounds of the present invention may be used as medicaments, e.g., in the form of pharmaceutical preparations which contain them mixed with a pharmaceutical, organic or inorganic inert carrier material which is suitable for enteral, percutaneous or parenteral application such as, e.g., water, gelatine, gum arabic, lactose, starch, magnesium stearate, talc, vegetable oils, polyalkylene glycols, Vaseline, etc. The pharmaceutical preparations can be in the solid form, e.g., as tablets, dragees, suppositories, capsules or in the liquid form, e.g., as solutions, suspensions or emulsions. If appropriate, they may be sterilized and/or contain adjuvants such as preservatives, stabilizers, wetting agents or emulsifying agents, salts for modifying the osmotic pressure and buffers. Additionally, they may contain other therapeutically valuable substances.

EXAMPLE 1

A solution of 147 mg of 17a-hydroxy-19-nor-D-homo-17a$\alpha$-pregna-5(10),9(11),16-trien-20-yn-3-one in 3 ml of methanol and 0.3 ml of conc. hydrochloric acid was stirred at 25° C for 30 minutes. The reaction mixture was neutralized with aqueous bicarbonate solution and distributed between ether and water. The crude product obtained after washing the organic phase with water, drying over magnesium sulfate and concentrating on a roller evaporator was purified by preparative thin-layer chromatography (Merck-Kiesel PSC finished plate F 254; hexane/ethyl acetate 2:1) and recrystallization from ethyl acetate to give pure 17a-hydroxy-D-homo-19-nor-17a$\alpha$-pregna-4,9,16-trien-20-yn-3-one, m.p. 199° C.

$[\alpha]_{589}^{25°\,C} -481°$ (dioxane; c = 0.100).

The starting material was prepared as follows:

A solution of 15 g of 3-methoxy-D-homoestra-1,3,5(10),16-tetraen-17a-one in 600 ml of glacial acetic acid and 375 ml of ca. 30% hydrobromic acid in glacial acetic acid was heated for 4 hours under reflux. The cooled, brown-green reaction mixture was concentrated and the residue distributed between dichloromethane and aqueous soda solution. The aqueous phase was extracted twice with dichloromethane and the organic phases were washed once with sodium carbonate solution and twice with water, dried over sodium sulfate and evaporated to dryness. Crystallization from ethyl acetate gave 3-hydroxy-D-homoestra-1,3,5(10),16-tetraen-17a-one, m.p. 261°–262° C.

$[\alpha]_{589}^{25°}$ $C$ +10° (dioxane; c = 0.083).

Hydrofluoric acid (40 ml) was initially added to a 100 ml polyethylene flask provided with a magnet stirrer and immersed in an ice-salt bath, antimony pentafluoride (14 ml) was added by pipette, with stirring (Bull. Chem. Soc. Fri. 1973, 1433). 3-Hydroxy-D-homoestra:1,3,5(10),16-tetraen-17a-one (10.6 g) was added portionwise, with stirring, at 20° C. The dark homogeneous solution was stirred for 6 hours at 0° C under argon in a closed system and then carefully added in portions to a mixture of ca. 220 g of sodium carbonate in 2 l of ice-water, with stirring. The aqueous alkaline phase was extracted twice with 500 ml of ether. The organic phases were separated, washed with ca. 500 ml each of water, dried over magnesium sulfate, combined and concentrated on a roller evaporator. The crude product was adsorbed on 450 g of Merck-Kieselgel 60 (0.06–0.2 mm). Elution with hexane/ethyl acetate (2:1) gave, after a few polar, non-uniform fractions, D-homoestra-4,9,16-trien-3,17a-dione, m.p. 118°–119° C (from ethyl acetate).

$[\alpha]_{589}^{25°}$ $C$ −295° (dioxane; c = 0.103).

p-Toluenesulfonic acid monohydrate (100 mg) was added to a solution of 2.3 g of D-homoestra-4,9,16-trien-3,17a-dione in 4 ml of abs. ethanol and 20 ml of ethyl orthoformate at ca. +5° C and the reaction mixture was stirred under argon for 60 minutes. Ether and aqueous bicarbonate solution were added to the reaction mixture and the organic phase was washed twice with water. The aqueous phases were separated and subsequently extracted twice with ether. After drying over magnesium sulfate and evaporating the organic phase, the residue was twice dissolved in benzene and evaporated yielding crude 3,3-diethoxy-D-homoestra-5(10),9(11),16-trien-17a-one as a yellow-brown resin.

A solution of 3.05 g of 3,3-diethoxy-D-homoestra-5(10),9(11), 16-trien-17a-one in 80 ml of abs. tetrahydrofuran was saturated with dry acetylene. Lithium acetylide-ethylenediamine complex (2.2 g) was added under an acetylene atmosphere and the mixture was stirred for 40 minutes at 25° C. The reaction mixture was diluted with ether and water was carefully added. The organic phase was washed twice with water and the aqueous phases were subsequently extracted twice with ether. After drying over magnesium sulfate and evaporation, crude 3,3-diethoxy-D-homo-19-nor-17aα-pregna-5(10),9(11),16-trien-20-yn-17a-ol was obtained as a yellow foam.

A solution of 0.6 g of oxalic acid in 24 ml of water was added to a solution of 3.1 g of 3,3-diethoxy-D-homo-19-nor-17aα-pregna-5(10),9(11),16-trien-20-yn-17a-ol in 64 ml of methanol, under argon. After stirring for 20 minutes at 25° C, the reaction mixture was neutralized with aqueous bicarbonate solution and distributed between ca. 300 ml of ether and a further ca. 150 ml of water. The organic phase was washed twice with water, the aqueous phases separated and subsequently extracted twice with ether. The organic phases were dried over magnesium sulfate and concentrated. Crystallization from ethyl acetate and silica gel chromatography of the mother liquor gave 17a-hydroxy-D-homo-19-nor-17aα-pregna-5(10),9(11),16-trien-20-yn-3-one, m.p. 180°–182° C (ethyl acetate).

$[\alpha]_{589}^{25°}$ $C$ −65° (dioxane; c = 0.102).

EXAMPLE 2

2,3-Dichloro-5,6-dicyano-1,4-benzoquinone (2 g) was added to a solution of 1.38 g of 17a-hydroxy-D-homo-19-nor-17aα-pregna-5(10),9(11),16-trien-20-yn-3-one in 140 ml of dichloromethane and the reaction mixture was stirred under argon for 60 minutes at 25° C. The reaction mixture was diluted with ca. 300 ml of ether, the (lighter) organic phase was washed twice with ca. 1M aqueous sodium bisulfate solution, three times with saturated aqueous potassium carbonate, twice with water and the aqueous phases were subsequently extracted twice with ether. After drying over magnesium sulfate and concentrating on a roller evaporator, the crude product was adsorbed on 40 g of silica gel (0.06–0.2 mm). Elution with hexane/ethyl acetate (2:1) gave 1.2 g of 17a-hydroxy-D-homo-19-nor-17aα-pregna-4,9,11,16-tetraen-20-yn-3-one, m.p. 205°–206° C (ethyl acetate).

$[\alpha]_{589}^{25°}$ $C$ −510° (dioxane; c = 0.102).

EXAMPLE 3

18-Methyl-D-homo-19-nor androsta-5(10),16-dien-17aβ-ol-3-one (2.0 g) was dissolved in 105 ml of pyridine and 2.32 g of pyridium bromide perbromide was added, with ice-cooling. The mixture was stirred for 4 hours, with ice-cooling, under argon and left for an additional 14 hours at −5° C in the refrigerator. The mixture was poured into 2N hydrochloric acid and extracted with ethyl acetate. 18-Methyl-D-homo-estra-4,9, 16-trien-17aβ-ol-3-one (1.46 g) m.p. 163°–165° C; $[\alpha]_D$ = −375° (CHCl$_3$) (CH$_2$Cl$_2$/isopropyl. ether 1:4), was obtained.

Preparation of the starting material:

A 20% solution of diisobutylaluminum hydride in toluene was added dropwise to a solution of 2.0 g of 3-methoxy-18-methyl-D-homo-estra-1,3,5(10),16-tetraen-17a-one in 30 ml of benzene, while flushing with argon and cooling with ice. The mixture was stirred for an additional 30 minutes at room temperature. Water (3ml) was subsequently carefully added, with cooling with ice, and the mixture was stirred for an additional 15 minutes at room temperature. The resulting precipitate was filtered and washed thoroughly with benzene. After concentrating the filtrate, 1.92 g of 3-methoxy-18-methyl-D-homo-estra-1,3,5(10),16-tetraen-17aβ-ol; m.p. 134°–136° C; $[\alpha]_D$ = +4.1° (CHCl$_3$), was obtained as colorless prisms from isopropyl ether/methylene chloride (4:1).

A solution of 4.5 g of 3-methoxy-18-methyl-D-homo-estra-1,3,5(10),16-tetraen-17aβ-ol in 90 ml of tetrahydrofuran and 10 ml of tert.-butanol was added dropwise to 220 ml of ammonia at −60° C. Lithium (2.25 g) was added over the course of 60 minutes and the mixture was stirred for an additional 3 hours at −50° to −60° C. Thereafter, ethanol was added dropwise to the reaction mixture until the blue color disappeared. The ammonia was allowed to evaporate, ca. 400 ml of saturated salt solution were added to the residue and the mixture was extracted with ether.

The crude product thus obtained was dissolved in 180 ml of acetone and 22 ml of water. After adding 3.6 g of oxalic acid, the mixture was stirred for 50 minutes at 40° C, subsequently poured into 500 ml of saturated sodium bicarbonate solution and extracted with ethyl acetate. After chromatography on aluminum oxide (neutral, Act. III) with petroleum/ethyl acetate (0–12%), 3.4 g of 18-methyl-D-homo-19-nor-androsta-5(10),16-dien-17aβ-ol-3-one, m.p. 123°–125° C (acetone/isopropyl ether, 1:8); $[\alpha]_D$ = +112.4° (benzene), was obtained.

EXAMPLE 4 a. Preparation of the starting material ca. 2N Methyllithium (7 ml) in ether was added to a solution of 2.5 g of 3,3-diethoxy-D-homo-estra-5(10),9(11),16-trien-17a-one in 100 ml of tetrahydrofuran at 0° C under argon. After stirring for 30 minutes at 0° C, water was carefully added and the mixture was extracted with ether. After washing with water, drying over magnesium sulfate and evaporating, 2.6 g of crude 3,3-diethoxy-17aβ-hydroxy-17aα-methyl-D-homo-estra-5(10),9(11),16-triene was obtained, 1.7 g of which was dissolved in 35 ml of methanol and 330 mg of oxalic acid in 13 ml of water added. After stirring under argon for 30 minutes, the mixture was neutralized with bicarbonate and distributed between ether and water. The ether phase was concentrated after washing with water and drying over magnesium sulfate.

b. The crude 17aβ-hydroxy-17a-methyl-D-homo-estra-5(10),9(11),16-trien-3-one thus obtained was dissolved in 100 ml of dichloromethane, 1.2 g of 2,3-dichloro-5,6-dicyanobenzoquinone was added and the mixture was stirred for 2 hours under argon. The dark green reaction mixture was distributed between ether and aqueous potassium carbonate solution and the ethereal phases were washed with water, dried over magnesium sulfate and concentrated. After chromatography of the crude product on 50 g of Kieselgel 60 (Merck, 0.06 — 0.2 mm) using dichloromethane containing 1% methanol as the eluent and crystallization from dichloromethane/ethyl acetate, 17aβ-hydroxy-17a-methyl-D-homo-estra-4,9,11,16-tetraen-3-one, m.p. 242°-245° C; $[\alpha]_{589}^{25°}$ $C$ $-601°$ (dioxane; c = 0.104), was obtained.

EXAMPLE 5 a. Preparation of the starting material ca. 1 Molar diisobutylaluminum hydride in toluene (12.2 ml) was added to a solution, stirred at 0° C, of 4.39 g of 3,3-diethoxy-D-homo-estra-5(10),9(11),16-trien-17a-one in 20 ml of toluene. After 30 minutes, water was carefully added and the precipitate was filtered over celite and carefully rinsed with ether. The organic phases were washed with water, dried over magnesium sulfate and evaporated to dryness. The residue was dissolved in 100 ml of methanol, a solution of 0.89 g of oxalic acid in 35 ml of water was added and the reaction mixture was stirred for 60 minutes at 25° C. After neutralization with bicarbonate solution, the reaction mixture was distributed between water and ether and the organic phases were washed with water, dried over magnesium sulfate and evaporated to dryness.

b. The crude 17aβ-hydroxy-D-homo-estra-5(10),9(11),16-trien-3-one so obtained was dissolved in 300 ml of dichloromethane, 4.2 g of 2,3-dichloro-5,6-dicyanobenzoquinone was added and the mixture was stirred for 30 minutes under argon. The reaction mixture was diluted with ether and initially washed with aqueous bicarbonate solution, then with water, dried over magnesium sulfate and evaporated to dryness. The residue gave, after silica gel chromatography (KG 60, Merck, 0.06-0.2 mm, dichloromethane with 1-3% methanol as the eluent) and crystallization from dichloromethane/ethyl acetate, 17aβ-hydroxy-D-homo-estra-4,9,11,16-tetraen-3-one; m.p. 215°-217° C.

$[\alpha]_{589}^{25°}$ $C$ $-505°$ (dioxane; c = 0.102).

EXAMPLE 6

Pyridinium bromide perbromide (44.6 g) was added to a solution of 34.5 g of 17aβ-hydroxy-D-homo-estra-5(10),16-dien-3-one in 1000 ml of pyridine at 0° C and the mixture was stirred for 16 hours at room temperature under argon. After removing the pyridine on a roller evaporator, the mixture was taken up in ether, washed once with aqueous hydrochloric acid, twice with water, dried over magnesium sulfate and evaporated. The residue was adsorbed on 1 kg of silica gel (0.06-0.2 mm). Elution with hexane/ethyl acetate (1:1) gave 17aβ-hydroxy-D-homo-estra-4,9,16-trien-3-one, m.p. 158°-159° C (dichloromethane/ether).

$[\alpha]_{589}^{25°}$ $C$ $-310°$ (dioxane; c = 0.102).

Preparation of the starting material:

A suspension of 62 g of copper(II) bromide in 40 ml of methanol and 30 ml of dichloromethane was added to a boiling solution of 44 g of 3-methoxy-D-homo-estra-1,3,5(10)-trien-17a-one in 100 ml of dichloromethane and 200 ml of methanol and the reaction mixture was stirred for 5 hours under reflux. The crystalline precipitate was filtered over Speedex and washed with dichloromethane and the filtrate was concentrated to dryness on a rotary evaporator. The residue was taken up in dichloromethane, washed three times with water and the aqueous phases were further extracted twice with dichloromethane. The organic phases were dried over sodium sulfate and concentrated on a rotary evaporator to yield 17β-bromo-3-methoxy-D-homo-estra-1,3,5(10)-trien-17a-one (crystallized from dichloromethane/hexane), m.p. 183° α 184° C.

$[\alpha]_D^{25°}$ $C$ $+32°$ (CHCl$_3$; c = 1.0).

Lithium bromide (43.5 g) and lithium carbonate (18.5 g) were added to a solution of 49 g of 17β-bromo-3-methoxy-D-homo-estra-1,3,5(10)-trien-17a-one in 400 ml of dimethylformamide and the mixture was stirred at a bath temperature of 110° C for 10 hours under argon. The reaction mixture was poured on to ice-water and extracted three times with dichloromethane. The organic extracts were rinsed twice with water, dried over sodium sulfate and concentrated on a rotary evaporator. The last traces of dimethylformamide were removed at 0.5 mm Hg/70° C. Crystallization from dichloromethane/acetone gave 3-methoxy-D-homo-estra-1,3,5(10),16-tetraen-17a-one, m.p. 161°-162° C.

$[\alpha]_D^{25°}$ $C$ $\pm 0°$ (CHCl$_3$; c = 1.0).

Lithium aluminum hydride (3.8 g) was added in portions to a solution of 36.5 g of 3-methoxy-D-homo-estra-1,3,5(10),16-tetraen-17a-one in 750 ml of abs. tetrahydrofuran, with stirring in an argon atmosphere at 0°-5° C. After stirring at 0° C for 2 hours, ethyl acetate and then ice-water were carefully added and the mixture was filtered over Speedex. The filtrate was extracted three times with ethyl acetate and the organic phases were washed twice with water, dried over sodium sulfate and concentrated to dryness on a roller evaporator. Crystallization of the crude product from ether/hexane gave 3-methoxy-D-homo-estra-1,3,5(10),16-tetraen-17aβ-ol, m.p. 100°-101° C.

$[\alpha]_D^{25°}$ $C$ $+28°$ (chloroform; c = 1.0).

A solution of 33 g of 3-methoxy-D-homo-estra-1,3,5(10),16-tetraen-17aβ-ol in 300 ml of abs. tetrahydrofuran and 300 ml of tert.-butanol was added dropwise to 750 ml of abs. liquid ammonia at −33° C over 15 minutes. Sodium (10.2 g) was added portionwise to the milky suspension. The dark blue mixture was stirred for 2 hours at −33° C, 100 ml of methanol were carefully added and the mixture was freed from ammonia by slowly warming to room temperature. The reaction mixture was poured on to ice-water and extracted with dichloromethane. The organic phases were washed twice with water, dried over sodium sulfate and evaporated to dryness on a roller evaporator. Crystallization from ether/hexane gave 3-methoxy-D-homo-estra-2,5(10),16-trien-17aβ-ol, m.p. 119°–120° C.

$[\alpha]_D^{25°\ C} +90°$ (chloroform; c = 1.0).

A solution of 5 g of oxalic acid in 50 ml of water was added to a solution of 53 g of 3-methoxy-D-homo-estra-2,5(10),16-trien-17aβ-ol in 200 ml of dichloromethane and 500 ml of methanol and the mixture was stirred for 2½ hours at 25° C. After neutralization by means of aqueous ammonium hydroxide, the methanol was removed on a roller evaporator and the aqueous residue was extracted with dichloromethane. The evaporation residue obtained after washing with water and drying over magnesium sulfate gave, after crystallization from dichloromethane/ether, 17aβ-hydroxy-D-homo-estra-5(10),16-dien-3-one, m.p. 151°–153° C.

$[\alpha]_{589}^{25°\ C} +152°$ (dioxane; c = 0.101).

EXAMPLE 7

A suspension of 1.80 g of 17aβ-acetoxy-18-methyl-3-pyrrolidino-D-homo-estra-3,5(10),9(11),16-tetraene in 5.2 g of 30% aqueous pyruvic acid was stirred for 10 minutes at 60° C under argon. The cooled solution was taken up in 50 ml of saturated sodium bicarbonate solution and extracted with ethyl acetate. After the customary work-up, 1.55 g of 17aβ-acetoxy-18-methyl-D-homo-estra-5(10),9(11),16-trien-3-one was obtained as a yellow oil which was dissolved without further purification in 55 ml of benzene and a solution of 2.0 g of 2,3-dichloro-5,6-dicyanobenzoquinone in 28 ml of benzene was added. The mixture was stirred for 15 hours at room temperature under argon, filtered and the filtrate was washed with 2 × 50 ml 1N sodium hydroxide solution, subsequently with saturated sodium chloride solution and concentrated in vacuo. The oily, yellow crude product was chromatographed on 70 g of silica gel with petroleum/ethyl acetate (0–16%) to give 17aβ-acetoxy-18-methyl-D-homo-estra-4,9,11,16-tetraen-3-one as a pale yellow oil.

Preparation of the starting material:

A solution of 2.5 g of 17aβ-hydroxy-18-methyl-D-homo-estra-4,9(10),16-trien-3-one in 7 ml of acetic anhydride and 1.5 ml of pyridine was stirred for 2.5 hours at 50° C under argon. The mixture was subsequently poured into ca. 100 ml of saturated sodium bicarbonate solution and extracted with 2 × 50 ml of ethyl acetate. The combined extracts were washed with sodium bicarbonate solution and sodium chloride solution, dried over sodium sulfate and concentrated in vacuo. After crystallization from ether/diisopropyl ether, 17aβ-acetoxy-18-methyl-D-homo-estra-4,9(10),16-trien-3-one, m.p. 140°–141° C, was obtained.

A solution of 1.95 g of 17aβ-acetoxy-18-methyl-D-homo-estra-4,9(10),16-trien-3-one in 5 ml of pyrrolidine was stirred under argon for 10 minutes at 100° C. After cooling, 20 ml of methanol was added and the mixture was allowed to crystallize at −5° C. The crystals were filtered and washed with ice-cold methanol. In this manner, 17aβ-acetoxy-18-methyl-3-pyrrolidino-D-homo-estra-3,5(10),9(11),16-tetraene was obtained as yellow needles, m.p. 131°–135° C.

EXAMPLE 8

A solution of 720 mg of 17aβ-acetoxy-18-methyl-D-homo-estra-4,9,11,16-tetraen-3-one in 30 ml of methanol was stirred, after adding 2.2 g of potassium carbonate, at room temperature for 60 minutes. The mixture was subsequently poured into 200 ml of water and extracted with ethyl acetate to give 17aβ-hydroxy-18-methyl-D-homo-estra-4,9,11,16-tetraen-3-one, m.p. 226°–228° C (diisopropyl ether.

$[\alpha]_D^{25°\ C} -514.8°$ (CHCl$_3$, c = 0.500).

EXAMPLE 9

A solution of 1 g of 17aα-ethynyl-3,3-ethylenedioxy-18-methyl-D-homo-5(10),9,(11),16-estratrien-17aβ-ol in 50 ml of methanol and 5ml of 2-N hydrochloric acid was stirred for 4 hours at 50° C under argon. After cooling, the mixture was poured into 300 ml of water, extracted with ethyl acetate and worked-up. There were obtained 890 mg of 17aα-ethynyl-17aβ-hydroxy-18-methyl-D-homoestra-4,9,16-trien-3-one; melting point 194°–196° C (from diisopropyl ether/methylene chloride); $[\alpha]_D^{25} = -502.9°$ (chloroform; c = 0.505).

The starting material was prepared as follows:

3 g of 18-methyl-D-homoestra-4,9,16-triene-3,17a-dione were heated in 60 ml of benzene and 12 ml of ethyleneglycol in the presence of 20 mg of p-toluenesulphonic acid for 7 hours while separating the water formed. After cooling, the mixture was poured into ca 100 ml of saturated sodium bicarbonate solution and extracted with ether. The ether extracts were dried over sodium sulphate and evaporated under reduced pressure. The residue was filtered over 80 g of aluminium oxide (neutral, activity III) [petroleum/ethyl acetate (0–10%)]. There were obtained 3.05 g of a light-yellow oil; $[\alpha]_D^{25} = -99.4°$ (benzene; c = 0.515).

Acetylene was passed through 136 ml of tetrahydrofuran for 30 minutes while cooling with ice, the tetrahydrofuran becoming saturated. 34 ml of a 15% solution of n-butyllithium in hexane and 35 ml of tetrahydrofuran were then added dropwise at 0° C and acetylene was conducted through the mixture for a further 45 minutes. Then, 2.7 g of 3,3-ethylenedioxy-18-methyl-D-homoestra-5(10),9(11),16-trien-17a-one in 108 ml of tetrahydrofuran were added dropwise and the mixture was stirred for 2 hours while cooling with ice. For the working-up, the mixture was treated dropwise with 40 ml of water and then poured into 400 ml of water. After extraction with ethyl acetate, drying the extract over sodium sulphate and evaporating, there were obtained 2.65 g of 17aα-ethynyl-3,3-ethylenedioxy-18-methyl-D-homoestra-5(10),9(11),16-trien-17aβ-ol; melting point 163°–165° C (from diisopropyl ether/methylene chloride).

1 g of 17aα-ethynyl-3,3-ethylenedioxy-18-methyl-D-homoestra-5(10),9(11),16-trien-17aβ-ol was stirred in 50 ml of 70% acetic acid for 5 hours at room temperature. The mixture was then poured into water and extracted with ethyl acetate. The organic extract was washed neutral with saturated sodium bicarbonate solution, dried over sodium sulphate and evaporated. There were obtained 910 mg of 17aα-ethynyl-17aβ-hydroxy-18-methyl-D-homoestra-5(10), 9(11), 16-trien-3-one; melting point 122°–124° C (from diisopropyl ether/methylene chloride).

EXAMPLE 10

700 mg of 17aα-ethynyl-17aβ-hydroxy-18-methyl-D-homoestra-5(10),9(11),16-trien-3-one in 30 ml of benzene were treated dropwise with a solution of 1.1 g of DDQ in 15 ml of benzene. The mixture was stirred at room temperature for 5 hours and then taken up in 100 ml of ethyl acetate. The ethyl acetate phase was washed three times with 50 ml of 1-N sodium hydroxide and with saturated sodium chloride solution, dried over sodium sulphate and evaporated. After filtration of the residue over ca 30 g of silica gel [petroleum/ethyl acetate (0–60%)], there were obtained 620 mg of 17aα-ethynyl-17aβ-hydroxy-18-methyl-D-homoestra-4,9,11,16-tetraen-3-one; melting point 175°–177° C (from diisopropyl ether/methylene chloride); $[\alpha]_D^{25} = -534.6°$ (chloroform; c = 0.505).

EXAMPLE 11

A solution of 1.1 g of 17aβ-hydroxy-18-methyl-D-homoestra-4,9,11,16-tetraen-3-one in 11 ml of tetrahydrofuran was treated with a few drops of phosphorus oxychloride and stirred for 24 hours at room temperature under argon. The mixture was then poured into saturated sodium bicarbonate solution and extracted with ether. The ether extracts were washed with saturated sodium chloride solution, dried over sodium sulphate and evaporated. The residue was chromatographed on ca 100 g of aluminum oxide (neutral, activity III) with petroleum/ethyl acetate (0–12%). There were obtained 1.2 g of 18-methyl-17aβ-tetrahydropyranyloxy-D-homoestra-4,9,11,16-tetraen-3-one as a colourless oil; $[\alpha]_D^{25} = -360.3°$ (benzene; c = 0.535).

EXAMPLE 12

A solution of 1.0 g of 3,3-diethoxy-D-homoestra-5(10),9(11),16-trien-17a-one in 20 ml of absolute benzene was treated with 4.2 ml of a 1 molar solution of diisobutylaluminium hydride in toluene. After stirring for 1 hour at 0° C, the mixture was poured into ice-cold dilute sodium hydroxide and extracted with ether. After the usual working-up, there were obtained 1.1 g of crude product which was dissolved in 20 ml of methanol and treated for 30 minutes with 2 ml of concentrated hydrochloric acid. The mixture was then neutralised with sodium bicarbonate, poured into water and extracted with ether. From the ether extract there was isolated 0.95 g of crude product which, after crystallisation from ethyl acetate/methylene chloride, gave pure 17aβ-hydroxy-D-homoestra-4,9,16-trien-3-one; melting point 158°–159° C; $[\alpha]_D^{25} = -310°$ (dioxan; c = 0.1); $\epsilon_{305} = 21,000$.

EXAMPLE 13

1.0 g of 17aα-ethynyl-17a-hydroxy-D-homoestra-4,9,16-trien-3-one was dissolved in 40 ml of toluene and 10 ml of pyridine and, after the addition of 0.5 g of 5% palladium/carbon catalyst, shaken with hydrogen until 1 equivalent of hydrogen had been taken up. The catalyst was filtered off and the solution evaporated in vacuo. The residue was recrystallised from ethyl acetate, there being obtained pure 17aβ-hydroxy-17a-vinyl-D-homoestra-4,9,16-trien-3-one; $\epsilon_{305} = 20500$.

EXAMPLE 14

In analogy to the process of Example 2, 17aβ-benzyloxy-D-homoestra-5(10), 9(11),16-trien-3-one was converted into 17aβ-benzyloxy-D-homoestra-4,9,11,16-tetraen-3-one, m.p. 120°–121° C (ether/hexane); $[\alpha]_{589}^{25} -248°$ (dioxane, c = 0.103).

The starting triene was prepared by reacting 17aβ-hydroxy-D-homoestra-4,9,16-trien-3-one with ethylene glykol and p-toluenesulfonic acid to yield 3,3-(ethylenedioxy)-D-homoestra-5(10),9(11),16 -trien-17aβ-ol, etherifying the latter with sodium hydride and benzyl chloride in tetrahydrofuran and hydrolyzing the ethylene ketal group with diluted acidic acid in an argon atmosphere.

EXAMPLE 15

In analogy to the process of Example 2, 17aβ-n-hexyloxy-D-homoestra-5(10),9(11),16-trien-3-one was converted into 17aβ-n-hexyloxy-D-homoestra-4,9,11,16-tetraen-3-one, $[\alpha]_{589}^{25} -328°$ (dioxane, c = 0.108).

EXAMPLE 16

17aβ-Acetoxy-D-homoestra-4,9,11,16-tetraen-3-one, $[\alpha]_{589}^{25} -330°$ (dioxane, c = 0.106) was obtained from 17aβ-hydroxy-D-homoestra-4,9,11,16-tetraen-3-one by treatment with acetic anhydride and pyridine.

EXAMPLE 17

17aβ-Propionyloxy-D-homoestra-4,9,16-trien-3-one was prepared from 17aβ-hydroxy-D-homoestra-4,9,16-trien-3-one by treatment with propionyl chloride and pyridine.

EXAMPLE 18

17aβ-Propionyloxy-D-homoestra-4,9,11,16-tetraen-3-one, m.p. 103–104° C, $[\alpha]_{589}^{25} -335°$ (dioxane, c = 0.100) was prepared from 17aβ-propionyloxy-D-homoestra-5(10), 9(11),16-trien-3-one in analogy to the process of Example 2.

EXAMPLE 19

17aβ-Undecanoyloxy-D-homoestra-4,9,11,16-tetraen-3-one, $[\alpha]_{589}^{25} -212°$ (dioxane, c = 0.108) was obtained from 17aβ-hydroxy-D-homoestra-4,9,11,16-tetraen-3-one by treatment with undecanoyl chloride and pyridine.

The following Example illustrates a typical pharmaceutical preparation containing one of the D-homosteroid provided by the present invention:

EXAMPLE A

A tablet for oral administration can contain the following ingredients:

| | |
|---|---|
| 17a-Hydroxy-D-homo-19-nor-17aα-pregna-4,9,11,16-tetraen-20-yn-3-one | 1 mg |
| Lactose | 60 mg |
| Maize starch | 37 mg |
| Talc | 1.8 mg |
| Magnesium stearate | 0.2 mg |
| Total weight | 100 mg |

We claim:
1. A compound of the formula

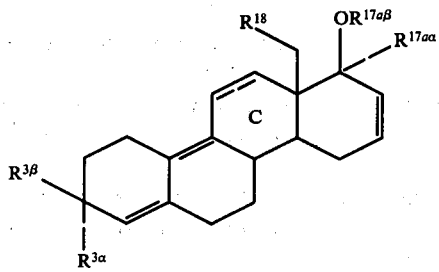

wherein $R^{3\alpha}$ is hydrogen, $R^{3\beta}$ is hydroxy, lower alkanoyloxy or aroyloxy and $R^{3\alpha}$ and $R^{3\beta}$ taken together are oxo; $R^{17a\alpha}$ is hydrogen, lower alkyl, ethynyl, vinyl, allyl, methallyl, propadienyl, 1-propynyl, butadiynyl or chloroethynyl; $R^{17a\beta}$ is hydrogen, alkanoyl, aroyl, lower alkyl, cycloalkyl-lower-alkyl, benzyl, furfuryl or tetrahydropyranyl; $R^{18}$ is hydrogen or methyl and the dotted line in the C-ring denotes an additional carbon to carbon bond in the 11,12-position.

2. The compound of claim 1 wherein $R^{3\alpha}$ and $R^{3\beta}$ taken together are oxo; $R^{17a\alpha}$ is hydrogen, lower alkyl or ethynyl and $R^{17a\beta}$ is hydrogen or lower alkanoyl.

3. The compound of claim 2 which is 17aβ-hydroxy-D-homo-19-nor-17aα-pregna-4,9,16-trien-20-yn-3-one.

4. The compound of claim 2 which is 17aβ-hydroxy-D-homo-19-nor-17aα-pregna- 4,9,11,16-tetraen-20-yn-3-one.

5. The compound of claim 2 which is 18-methyl-D-homoestra-4,9,16-trien-17aβ-ol-3-one.

6. The compound of claim 2 which is 17aβ-hydroxy-17a-methyl-D-homoestra-4,9,11,16-tetraen-3-one.

7. The compound of claim 2 which is 17aβ-hydroxy-D-homoestra-4,9,11,16-tetraen-3-one.

8. The compound of claim 2 which is 17aβ-hydroxy-D-homoestra-4,9,16-trien-3-one.

9. The compound of claim 2 which is 17aβ-acetoxy-18-methyl-D-homoestra-4,9,11,16-tetraen-3-one.

10. The compound of claim 2 which is 17aβ-acetoxy-18 -methyl-D-homoestra-4,9,16-trien-3-one.

11. The compound of claim 2 which is 17aβ-hydroxy-18-methyl-D-homoestra-4,9,11,16-tetraen-3-one.

12. The compound of claim 2 which is 17aα-ethynyl-17aβ-hydroxy-18-methyl-D-homoestra-4,9,16-trien-3-one.

13. The compound of claim 2 which is 17aα-ethynyl-17aβ-hydroxy-18-methyl-D-homoestra-4,9,11,16-tetraen-3-one.

14. The compound of claim 1 wherein $R^{3\alpha}$ and $R^{3\beta}$ taken together are oxo, $R^{17a\alpha}$ is hydrogen, lower alkyl or ethynyl and $R^{17a\beta}$ is vinyl.

15. The compound of claim 14 which is 17aβ-hydroxy-17a-vinyl-D-homoestra-4,9,16-trien-3-one.

16. The compound of claim 1 which is 18-methyl-17aβ-tetrahydropyranyloxy-D-homoestra-4,9,11,16-tetraen-3-one.

* * * * *